(12) United States Patent
Steemers et al.

(10) Patent No.: US 8,202,691 B2
(45) Date of Patent: Jun. 19, 2012

(54) UNIFORM FRAGMENTATION OF DNA USING BINDING PROTEINS

(75) Inventors: Frank Steemers, Encinitas, CA (US); Jonathan Mark Boutell, Essex (GB)

(73) Assignee: Illumina, Inc., San Diego, CA (US)

( * ) Notice: Subject to any disclaimer, the term of this patent is extended or adjusted under 35 U.S.C. 154(b) by 583 days.

(21) Appl. No.: 12/357,995

(22) Filed: Jan. 22, 2009

(65) Prior Publication Data
US 2009/0191563 A1    Jul. 30, 2009

Related U.S. Application Data

(60) Provisional application No. 61/023,770, filed on Jan. 25, 2008.

(51) Int. Cl.
C12P 19/34    (2006.01)
C07H 21/02    (2006.01)
C07H 21/04    (2006.01)

(52) U.S. Cl. ............... 435/6.12; 536/23.1; 536/24.2; 536/24.33

(58) Field of Classification Search .................. None
See application file for complete search history.

(56) References Cited

U.S. PATENT DOCUMENTS

| 6,023,540 | A | 2/2000 | Walt et al. |
|---|---|---|---|
| 6,200,737 | B1 | 3/2001 | Walt et al. |
| 6,327,410 | B1 | 12/2001 | Walt et al. |
| 6,355,431 | B1 | 3/2002 | Chee et al. |
| 6,429,027 | B1 | 8/2002 | Chee et al. |
| 6,482,593 | B2 | 11/2002 | Walt et al. |
| 6,787,308 | B2 | 9/2004 | Balasubramanian et al. |
| 7,115,400 | B1 | 10/2006 | Adessi et al. |
| 7,754,429 | B2 * | 7/2010 | Rigatti et al. ............ 435/6 |
| 2002/0102578 | A1 | 8/2002 | Dickinson et al. |
| 2003/0108900 | A1 | 6/2003 | Oliphant et al. |
| 2005/0042649 | A1 | 2/2005 | Balasubramanian et al. |
| 2005/0100900 | A1 | 5/2005 | Kawashima et al. |
| 2005/0181394 | A1 | 8/2005 | Steemers et al. |
| 2006/0040297 | A1 * | 2/2006 | Leamon et al. ............ 435/6 |
| 2006/0275782 | A1 | 12/2006 | Gunderson et al. |
| 2007/0128624 | A1 | 6/2007 | Gormley et al. |
| 2008/0009420 | A1 | 1/2008 | Schroth et al. |
| 2008/0242560 | A1 | 10/2008 | Gunderson et al. |

FOREIGN PATENT DOCUMENTS

WO    WO 0018957 A1 *    4/2000

(Continued)

OTHER PUBLICATIONS

Azzoni et al. Using archaeal histones for precise DNA fragmentation. Protein Engineering, Design & Selection 20(6):267-271 (published online May 31, 2007).*

(Continued)

*Primary Examiner* — Samuel Woolwine
(74) *Attorney, Agent, or Firm* — John T. Murphy

(57) ABSTRACT

The invention provides a method for preparing and analysing a population of fragmented polynucleotide sequences having a substantially uniform size. The method can include steps of (a) binding at least one protection molecule to at least one polynucleotide sequence; (b) cleaving the at least one polynucleotide sequence to generate a plurality of polynucleotide fragment sequences of substantially uniform size; (c) amplifying the polynucleotide fragments; and (d) determining a sequence characteristic of a plurality of the polynucleotide fragments.

19 Claims, 3 Drawing Sheets

← Trinucleosome
← Dinucleosome
← Mononucleosome

FOREIGN PATENT DOCUMENTS

| WO | 03/074734 | 9/2003 |
| --- | --- | --- |
| WO | 2007/010251 | 1/2007 |
| WO | 2007/010252 | 1/2007 |
| WO | 2007/091077 | 8/2007 |
| WO | 2008/041002 | 4/2008 |
| WO | 2009/032167 | 3/2009 |

OTHER PUBLICATIONS

Zacchi et al. Selecting open reading frames from DNA. Genome Research 13:980-990 (2003).*

Chrysogelos, Susan et al., "*Escherichia coli* Single-Strand Binding Protein Organizes Single-Stranded DNA to Nucleosome-Like Units", PNAS, vol. 79, 1982, 5803-5807.

Grayling, et al., "DNA binding and nuclease protection by the HMf histones from the hyperthermophilic archaeon *Methanothermus fervidus*", Extremophiles. May 1997;1(2):79-88, Department of Microbiology, The Ohio State University.

Lohman, Timothy M. et al., "Two Binding Modes in *Escherichia coli* Single Strand Binding Protein-Single Stranded DNA Complexes", The Journal of Biological Chemistry, vol. 260 (6), 1985, 3594-3603.

* cited by examiner

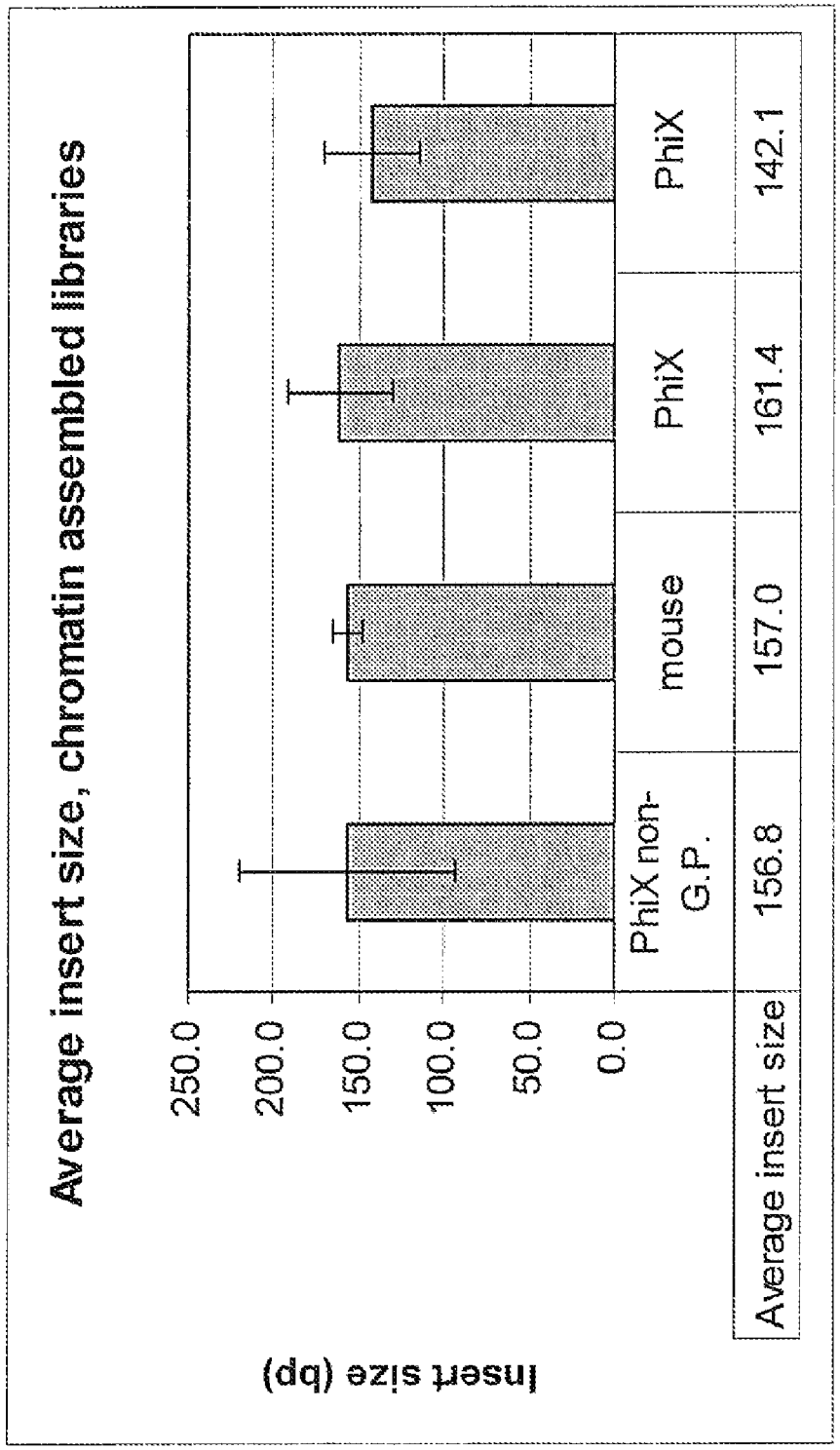

UNIFORM FRAGMENTATION OF DNA USING BINDING PROTEINS

This application is: based on, and claims the benefit of, U.S. Provisional Application Ser. No. 61/023,770, filed Jan. 25, 2008 and entitled "Uniform Fragmentation of DNA Using Binding Proteins," the entirety of which is hereby incorporated by reference.

FIELD OF THE INVENTION

This invention relates to the use of binding proteins or nucleic acid scaffolds such as histosnes, for the preparation of uniform length fragments of nucleic acids. The invention is particularly useful in the preparation of nucleic acid libraries for amplification and sequencing applications.

BACKGROUND TO THE INVENTION

The ability to acquire and analyse DNA sequence data has increased phenomenally over the past few years. As a result, nucleic acid analysis has become increasingly important in many areas of biology, biotechnology and medicine.

New sequencing technologies such as those based on sequencing by synthesis have the ability to produce raw sequence data at a rate and quantity many orders of magnitude higher than previously possible with Sanger sequencing and other conventional methods. However, there are a number of important differences in the sequence data that is produced. Whilst the introduction of new sequencing technologies has led to a significant increase in the amount of raw nucleic acid sequence obtained, there has also been a concomitant reduction in read length. Despite this, in terms of sequence assembly it is now possible to produce high depth sequence data for a medium sized genome from just a single sequencing run.

The starting point for many nucleic acid analyses is genomic DNA which may contain tens of millions of base pairs. Therefore, fragmentation of the nucleic acid sequence is generally required to reduce the size of the sequence into smaller parts that are more amenable to manipulation.

Fragmentation of nucleic acids is generally performed by enzymatic, chemical or mechanical means. A primary disadvantage of each of these methods is that although the nucleic acid may be randomly fragmented, the resulting fragments are distributed across a wide range of sizes. As a result, further purification steps such as gel purification are required to select fragments of suitable size for a particular application. Since new sequencing technologies generally provide shorter read lengths, the use of larger fragments is less efficient both it terms of sequence coverage and utilisation of material, for example. Size selection based on electrophoresis and gel excision of the desired size range leaves the bulk of the starting nucleic acid in the electrophoresis gel.

There is a need for sample preparation methods where the sample is treated to obtain material of a desired length, and all of the sample is available for subsequent use, especially in cases where the amount of material is limited, such as biopsies, laser captured cells, limited archival tissues, embryoid bodies small model systems, and difficult to cultivate organisms such as Microsporidia. The present invention satisfies this need and provides other advantages as well.

SUMMARY OF THE INVENTION

In a first aspect the invention provides a method for preparing and analysing a population of fragmented polynucleotide sequences having a substantially uniform size. The method can include steps of (a) binding at least one protection molecule to at least one polynucleotide sequence; (b) cleaving the at least one polynucleotide sequence to generate a plurality of polynucleotide fragment sequences of substantially uniform size; (c) amplifying the polynucleotide fragments; and (d) determining a sequence characteristic of a plurality of the polynucleotide fragments.

The invention also provides a method for preparing and analysing a population of fragmented polynucleotide sequences having a substantially uniform size. The method can include the steps of (a) binding at least one protection molecule to at least one polynucleotide sequence; (b) cleaving the at least one polynucleotide sequence to generate a plurality of polynucleotide fragment sequences of substantially uniform size; (c) removing the protection molecule from the polynucleotide fragment sequences; (d) attaching universal sequences to the ends of each polynucleotide fragment; (e) amplifying the polynucleotide fragments; and (f) sequencing the polynucleotide fragments, thereby analysing a population of fragmented polynucleotide sequences having a substantially uniform size.

The invention further provides a method for preparing an array of fragmented polynucleotide sequences having a substantially uniform size. The method can include the steps of (a) binding at least one protection molecule to at least one polynucleotide sequence; (b) cleaving the at least one polynucleotide sequence to generate a plurality of polynucleotide fragment sequences of substantially uniform size; (c) amplifying the polynucleotide fragments, thereby producing amplified products of the fragments; and (d) attaching a plurality of the polynucleotide fragments or the amplified products to an array.

The steps of the method can be carried out in any of a variety of orders. For example, the plurality of the polynucleotide fragments can be attached to the array before or after amplifying the fragments.

A second aspect of the invention relates to the use of protection molecule for the preparation of polynucleotide sequence fragments having a substantially uniform size for paired end sequencing.

A third aspect of the invention relates to a library of nucleic acid fragments of substantially uniform size containing known sequence ends.

BRIEF DESCRIPTION OF THE DRAWINGS

FIG. 3 shows that even without gel purification of the library, the fragment size is: reasonably well controlled.

DETAILED DESCRIPTION OF THE INVENTION

Figure 1:
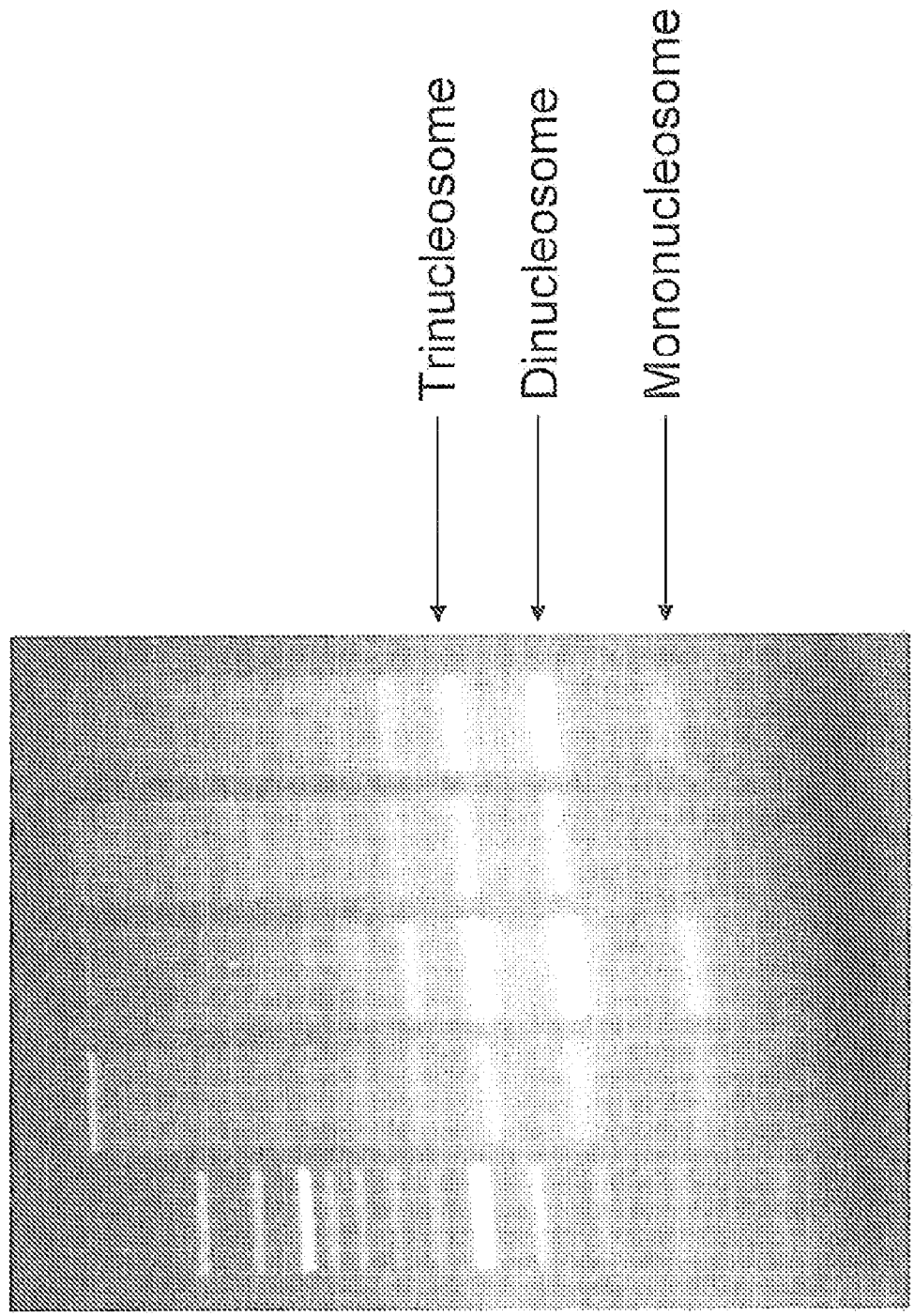
FIG. 1 shows a gel having bands of certain sizes produced by chromatin assembly and partial enzymatic digestion of nucleic acid sequences

The Invention relates to methods of generating fragments of one or more polynucleotide molecules having a substantially uniform size range and, more particularly, which does not require size selection by a size separation method such as gel purification. Particularly the fragments can be used in sequencing by synthesis methods that give rise to paired end information where a read is obtained from both ends of the fragments.

Sample preparation methods where all of the sample is treated to obtain material of a certain length, and all of the sample is available for subsequent use, is especially advantageous to samples where the amount of material is limited, such as biopsies, laser captured cells, limited archival tissues, embryoid bodies, small model systems, and difficult to cultivate organisms such as Microsporidia.

Thus the invention provides a method of nucleic acid fragmentation that produces fragments of a defined size and that are therefore better suited for use with new sequencing technologies such as sequencing by synthesis. Fragments of known size are especially advantageous when sequencing from both ends of each fragment. Such paired end reads allow for accurate placement of the empirically derived sequence of a fragment within the reference sequence for a genome of interest. The more tightly controlled the size distribution, the more accurate the paired end information obtained. For example, if the length of each of the fragments in the sample is exactly 150 bases, then it is possible to work out whether the sample of interest has an insertion or deletion mutation anywhere in the 150 bases simply by sequencing the two ends. If the reads from each end of the fragment are only 149 bases apart in the reference genome, then the sample known to be exactly 150 bases apart due to the sample preparation process must have undergone an insertion mutation. Likewise if the two fragments are 151 bases apart in the reference genome, the process giving rise to known 150 mers shows that the sample of interest has had a base deleted and is therefore shorter than the reference. The accurate control of size distribution of nucleic acid fragments is therefore of great importance for paired end sequencing.

The methods set forth herein exploit the surprising discovery that protein scaffolds such as histones or nucleic acid binding proteins can be used to produce nucleic acid fragments of a tightly defined size that can subsequently be utilised, for example, in the preparation of nucleic acid libraries for sequencing. Assembly of DNA into chromatin is usually used to study the function of DNA in its native environment, for example, by carrying out in-vitro studies of factors affecting initiation of DNA transcription. DNA binding proteins play essential roles in DNA replication, recombination and repair. Recently DNA binding proteins have been used to improve the efficiency of the Polymerase Chain Reaction (PCR).

Although chromatin assembly and nucleosomes have been used to study the molecular mechanisms of DNA directed processes, the use of nucleosome formation methods for the purpose of uniform fragmentation of nucleic acids for sequencing has not been described prior to the disclosure of the present invention. The methods described herein are based, at least in part, on the discovery that nucleic acids removed from nucleosomes or binding proteins can be efficiently utilised in sequencing by synthesis, particularly methods using cluster formation. Because digestion of nucleic acids bound to chromatin yields predictable and uniform fragmentation, it is especially suitable for methods of nucleic acid library formation, cluster formation and sequencing where use of a broad range of DNA lengths is undesirable.

As used herein, the term 'polynucleotide' refers to deoxyrribonucleic acid (DNA), ribonucleic acid (RNA) or analogue thereof. The term should be understood to include, as equivalent, analogues of either DNA or RNA made from nucleotide analogues and to be applicable to single stranded (such as sense or antisense) and double stranded polynucleotides. The term as used herein also encompasses cDNA, that is complementary or copy DNA produced from an RNA template, for example by the action of reverse transcriptase.

The polynucleotide molecules may originate in double-stranded DNA (dsDNA) form (e.g. genomic DNA, PCR and amplification products and the like) or may have originated in single stranded form as DNA or RNA and may be converted to dsDNA form and vice-versa. The precise sequence of the polynucleotide molecules may be known or unknown.

In a particular embodiment the polynucleotide molecules are DNA molecules. More particularly the polynucleotide molecules can represent the entire genetic complement of an organism and can be genomic DNA molecules which include both intron and exon sequence (coding sequence), as well as non-coding regulatory sequences such as promoter and enhancer sequences. It could also be envisaged that particular subsets of polynucleotide sequencers from a sample such as a genomic DNA sample could also be used, such as particular chromosomes for example. Yet more particularly, the sequence of the primary polynucleotide molecules can be unknown for one or more steps of a method set forth herein. Still yet more particularly, the primary polynucleotide molecules can be human genomic DNA molecules.

The polynucleotide molecule may comprise a single polynucleotide molecule or a mixture of polynucleotide molecules prepared by mixing a plurality, greater than one, of individual polynucleotide molecules. For example, DNA from more than one source, can be prepared. It may also be envisaged that such DNA samples stay be tagged to determine its source after it has been sequenced. Many different suitable DNA-tag methodologies exist in the art and are well within the purview of the skilled person, including for example, those described in U.S. Pat. No. 5,846,719 or WO 05/068656 A1, each of which is incorporated herein by reference.

The term 'substantially uniform size,' when used in reference to polynucleotide fragments, is used to refer to a population of polynucleotide fragments wherein a majority of the fragments have the same length within an acceptable variance for a subsequent analysis of the population. For example, the range of variance can be acceptable for the assumption that all fragments sequenced in a sequencing-by-synthesis method have the same length. The population can be a single population in a sample or a subpopulation within a sample. In particular embodiments, the acceptable variance for the length of an given fragment in the population or subpopulation can be at most 10%, 8%, 5%, 2%, 1% or 0.1% Of the average length for fragments in the population. This can be a variance in length of at most about 1, 2, 3, 4, 5 or 10 nucleotides. The population can be composed of at least 90%, 95%, 99% or 99.9% fragments having a particular length.

Fragments of substantially uniform size can be obtained following, for example, enzymatic digestion of chromatin or nucleic acids protected by other binding proteins Fragmentation of nucleic acids not assembled into chromatin ('naked' nucleic acid) produces a wide range of fragment sizes appearing as a smear of nucleic acids when run on a gel. In particular embodiments, a population can be produced having two or more subpopulations each of a substantially uniform size. For example, three different subpopulations are shown in the gel of FIG. 1 being produced from the mono-, di- and tri-nucleosome protected products of a DNA cleavage reaction with micrococcal nuclease.

The human genome consists of several metres of DNA compacted within the nucleus of a cell having an average diameter of ~10 um. In the eukaryote nucleus, DNA is packaged into a nucleoprotein complex known as chromatin. The basic repeating unit of chromatin is the nucleosome which typically consists of about 146 base pairs of DNA wrapped approximately 1.7 times around a core histone octamer. The histone octamer consists of two copies of each of the histones H2A, H2B, H3 and H4. Nucleosomes are regularly spaced along the DNA in the manner of beads on, a string. The spacing of the nucleosomes is not dependent upon any variations in the DNA sequence itself, and therefore if the 'string' can be cut between each 'bead' then the length of the fragments remaining after the digestion should be the length of the 'bead' of the nucleosome complex, namely around 146 base pairs. Fragments of this length serve as an ideal basis for short read, high throughput sequencing methods that determine a paired read from both ends of each fragment.

As used herein the term 'protection molecule' means a molecule that is capable of binding to a portion of a polynucleotide to prevent cleavage of the portion under conditions where another portion of the polynucleotide is cleaved. An exemplary protection molecule is a histone or complex of histones. Any protein that binds in a non sequence specific manner to either single stranded or double stranded nucleic acids can be used in a method of the invention. The protein can simply bind to the nucleic acid sample stably enough under conditions where portions of the nucleic acids that are not bound to the protein are digested and at least one portion of the nucleic acid that is bound to the protein is not digested. Binding proteins and other scaffold proteins may be used to protect lengths of nucleic acids from, for example, enzymatic digestion. For example) binding of single stranded DNA binding protein (SSB) to single stranded DNA can protect a 'footprint' of ~30-90 bp of DNA from enzymatic digestion.

Fragmentation of the chromatin can be performed with an enzyme shearing cocktail, containing for example micrococcal nuclease, which cleaves both strands of DNA in the linker region between protein protected regions, such as nucleosomal cores. For example, nuclease cleavage of DNA having attached nucleosomal cores leaves the part of the DNA coiled around the core histone octamer intact. Digestion of chromatin generally results in mono-nucleosomal fragments having DNA fragment sizes of ~146 bp. Di-nucleosomal fragments have DNA fragment sizes of ~300 bp comprising two nucleosome cores linked by a linker region of undigested DNA.

Thus, in Contrast to enzymatic digestion of raw nucleic acids, fragmentation of chromatin by, for example, enzymatic digestion, results in a ladder of distinct bands when run on a gel. In this case, the smallest nucleic acid fragments of the ladder have a size corresponding to the unit of one nucleosome (1N). Other such fragments are dimers (2N+L), trimers (3N+2L) . . . etc. Where N is the number of base pairs of nucleic acid per nucleosome core and L is the length of nucleic acid linker in 'string' of non-nucleosomal base pairs. Thus generally speaking for any 'X' I-mer the expected length of nucleic acid in base pairs can be generalised as $XN+(1-X)L$. It should be noted that this prediction is a generalisation and the skilled person will be aware that there will be minor variations in nucleic acid fragment length due to variations in linker size, for example.

Fragmentation of polynucleotide molecules with parts protected by proteins such as histones assembled into chromatin may be carried out by fragmentation methods known in the art. For example, mechanical means (such as nebulisation, sonication and hydroshear), chemical Means or enzymatic means. Any fragmentation method that is selective for portions of polynucleotides not bound to protection molecules, leaving bound portions intact can be used.

Subpopulations of polynucleotides having substantially uniform size typically produce specific bands of a generally predictable and similar size range rather than as a 'smear' or broad variation of sizes in an electrophoresis gel.

A polynucleotide sample used in a method set forth herein can include one or more bound proteins such as histones. Alternatively, a polynucleotide can be purified from other components of its native milieu or can be a copy amplified from a native sample. Broadly, two methods have been developed for in-vitro assembly of chromatin—one ATP-independent, the other ATP-dependent. ATP-independent assembly utilises core histones, DNA and a histone chaperone (for example, NaCl or NAP-1) and results in a random arrangement of histones on the DNA. ATP-dependent assembly requires the use of ATP-utilising chromatin assembly factors such as ACF or RSF and results in periodic nucleosome arrays.

It should be noted that chromatin with a random arrangement of histones may contain stretches of 'naked' nucleic acid, that is stretches not protected from digestion. Hence, in this case any fragmentation of such chromatin will result in a greater variance or range of the number of different fragments in the population following nuclease treatment. However, the size of those fragments protected by histones will remain predictable.

Accordingly, a population of polynucleotide fragments can be characterized not only by the size of the fragments (i.e. sequence length) but additionally or alternatively it can be characterized by the number of fragments of different sequence in the population. A population of polynucleotide fragments can include a sequence representation that includes all or part of the original sequence from which it was derived Preferably the fragmentation of a polynucleotide molecule will be random, that is, fragments are produced in a non-ordered fashion. A sample having multiple copies of the same sequence, such as a genomic DNA sample obtained from many cells of the same organism or amplified to produce multiple copies, when randomly fragmented by the methods set forth herein, can yield a population of fragments that includes substantially the entire sequence complement of the genome albeit broken up into smaller lengths. However, fragmentation may also be generally non-random such that the fragments produced by the method are broadly directed to or enriched for specific features such as promoter regions and other regulatory sequences. Thus, in this case, the use of particular DNA binding proteins is of particular utility in the production of libraries of fragments enriched for such features. For example, one or more species of transcription factor proteins can be bound to DNA and the DNA cleaved to produce fragments having transcriptional regulatory sequences or other sequences that bind to the transcription factors. In this case all other sequences in the genome that do not bind to the transcription factor protein(s) will be digested, thereby being excluded from subsequent analysis. The protein sample used to protect a polynucleotide sample during nuclease digestion cat consist of a homogeneous population having only one species or type of protein. Alternatively, a protein sample having a mixture of different nucleic acid binding proteins can be used such as a mixture of many different transcription factors that are specific for A variety of different regulatory sequences.

Further examples of proteins that can be used to protect portions of a polynucleotide sample to produce polynucleotide fragments include transcription regulators, transcription activators and transcription initiators. Such proteins are often classified according to their DNA binding motif be they, helix-turn-helix, zinc binding, leucine zipper or beta hairpin/ribbon motifs. Accordingly, proteins engineered to have such motifs that are capable of stably binding to nucleic acids can be used in accordance with the methods set forth herein.

The proteins used to protect the polynucleotides can be modified from their native state to have a desired binding property such as increased, deceased or changed sequence specificity. The footprint (i.e. size of the protected sequence region) can be altered, for example, to be larger by crosslinking several protein molecules together or genetically engineering the protein to be larger. Similarly, the footprint for a protein can be reduced by proteolyzing the protein to make it smaller or genetically engineering a deletion fragment of the protein. Such modified proteins can be created using known methods and screened in a DNA binding assay for desired binding properties, using routine methods. Additionally or alternatively, binding conditions can be altered to change the size of the footprint for a given protein. For example, changes in salt concentration, pH, or temperature can be used to change the footprint size and hence the size of fragments produced by the methods: set forth herein.

In particular embodiments, conditions can be selected that result in more stable binding of a protein to nucleic acids. For example, changes in pH, ionic strength and or polarity of the solution can be altered. If desired, the proteins can be crosslinked to nucleic acids, preferably using a reversible or cleavable crosslinking reagent. Following fragmentation of the nucleic acid, the crosslink can be disrupted, yielding a nucleic acid sample that is capable of being amplified or analyzed directly for one or more sequence characteristics. Reversible crosslinking can be achieved using formaldehyde which introduces a methylene bridge that can be cleaved by mild heating or sonication (see Hayat *Principles and Techniques Of Electron Microscopy: Biological Applications* 4$^{th}$ Ed. Cambridge University Press (2000)) Reversible bi-metallic crosslinking reagents can also be used as described, for example in U.S. Pat. No. 5,534,542.

In some embodiments, it may be desirable to remove the proteins from the polynucleotides, for example, after nuclease cleavage has been carried out. Histones or other proteins can be digested with a protease, for example proteinase K, prior to use of the nucleic acid fragments. Proteins can also be removed from the polynucleotide fragments using known methods such as denaturation, extraction, or chromatography. For example, the fragments may be gel purified. If desired the polynucleotide fragments can be used directly without purification to remove proteins, as shown in FIG. 3.

Such fragmentation may result in fragmented polynucleotide sequences with a heterogenous mix of blunt and 3' and 5' overhanging ends. It is therefore desirable to repair the fragment ends using methods or kits known in the art to generate ends that are convenient, for example, for insertion into blunt sites in cloning vectors or for ligation of adapters onto the ends of each fragment.

Template Libraries

In particular embodiments, template libraries may be prepared from the fragmented polynucleotide sequences. Following end repair, double stranded adaptor polynucleotide sequences may be ligated to both ends of the fragmented polynucleotide sequences to form adaptor-fragment-adaptor polynucleotide sequences. It is particularly advantageous to use the same adaptor construct for both ends of the adaptor-fragment-adaptor duplex, although two sets of adaptors can also be utilised.

Ligation methods are known in the art and utilise standard methods (Sambrook and Russell, Molecular Cloning, A Laboratory Manual, third edition Cold Spring Harbor Laboratory Press (2001)). Such methods utilise ligase enzymes such as DNA ligase to effect or catalyse joining of the ends of the two polynucleotide strands of, in this case, the adaptor duplex construct and the target polynucleotide duplexes, such that covalent linkages are formed. The adaptor duplex construct May contain a 5'-phosphate moiety in order to facilitate ligation to the target 3'-OH. The target contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. Generally such joining takes place by formation of a phosphodiester linkage between the two polynucleotide strands, but other means of covalent linkage (e.g. non phosphodiester backbone linkages) may be used.

The adaptor constructs may also contain a region on one, or both, of the strands that does not hybridise with a sequence on the other strand of the adaptor. Such 'mismatched' adaptors can serve as priming sites for amplification reactions, and may allow for amplification with primers extending beyond the sequence of the ligated adaptor. Ligation of mismatched adapters is described in copending application US 2007/0128624, whose contents are included herein by reference. Optionally the adaptor-fragment-adaptor sequences may be purified from any components of the ligation reaction, such as enzymes, buffers, salts and the like. Suitable purification methods are known in the art and utilise standard methods (Sambrook and Russell, Supra).

In further embodiments the adaptor-fragment-adaptor sequences may be amplified. The contents of an amplification reaction are known by one skilled in the art and include appropriate substrates (such as dNTPs), enzymes (e.g. a DNA polymerase) and buffer components required for an amplification reaction. Generally amplification reactions use at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus the primer oligonucleotides include a sequence of nucleotides capable of annealing to a part of, that is, a primer-binding sequence, in the adaptor-fragment-adaptor polynucleotide sequences to be amplified (or the complement thereof if the template is viewed as a single strand) during the annealing step.

The forward and reverse primers may be of sufficient length to hybridise to the whole of the adaptor sequence and at least one base of the target sequence. The forward and reverse primers may also contain a region that extends beyond the adaptor construct, and therefore the amplification primers may be at least 20-100 bases in length. The forward and reverse primers may be of significantly different lengths; for example one may be 20-40 bases, and one may be 40-100 bases in length. The nucleotide sequences of the forward and reverse primers are selected to achieve specific hybridisation to the sequences to be amplified under the conditions of the annealing steps of the amplification reaction, whilst minimising non-specific hybridisation to any other sequences present. Skilled readers will appreciate that it is not strictly required for the primer-binding sequence to be 100% complementary, a satisfactory level of specific annealing can be achieved with less than perfectly complementary sequences. In particular, one or two mis-matches in the adaptor-target specific portion can usually be tolerated without adversely affecting specificity for the template.

The term "library" refers to a collection or plurality of molecules. The molecules can be polynucleotides with different sequences. However, a portion of the polynucleotides can have the same sequence. For example, the different polynucleotides in a library can share common sequences at their 5' ends and common sequences at their 3' ends. Use of the term "library" to refer to a collection or plurality of polynucleotide template molecules should not be taken to imply that the templates making up the library are derived from a particular source, or that the "library" has a particular composition. By way of example, use of the term "library" should not be taken to imply that the individual templates within the library must be of different nucleotide sequence or that the templates be related in terms of sequence and/or source.

In it's various embodiments the invention encompasses formation of so-called "monotemplate" libraries, which comprise multiple copies of a single type of template molecule, each having common sequences at their 5' ends and their 3, ends, as well as "complex" libraries wherein many, if not all, of the individual template molecules comprise different target sequences (as defined below), although all library members share common sequences at their 5' ends and 3, ends. The 5' ends may be the same as the 3' ends, or may be of unrelated, different sequences. Such complex template libraries may be prepared from fragmented polynucleotide sequences as described above and starting from a complex mixture of target polynucleotides such as (but not limited to) random genomic DNA fragments, cDNA libraries etc. The invention also extends to "complex" libraries formed by mixing together several individual "monotemplate" libraries, each of which has been prepared separately starting from a single type of target molecule (i.e. a monotemplate). In preferred embodiments more than 50%, or more than 60%, or more than 70%, or more: than 80%, or more than 90%, or more than 95% of the individual polynucleotide templates in a complex library may comprise different target sequences, although all templates in a given library can share common sequence at their 5' ends and common sequence at their 3' ends.

Use of the term "common" is interpreted as meaning common to all molecules in the library. As explained above, all polynucleotide templates within the library can contain regions of common sequence at (or proximal to) their 5' and 3' ends, wherein the common sequence at the 5' end of each individual template in the library is not identical and not fully complementary to the common sequence at the 3' end of said template.

Use of the term "template" to refer to individual polynucleotide molecules in the library merely indicates that one or both strands of the polynucleotides in the library are capable of acting as templates for template-dependent nucleic acid polymerisation catalysed by a polymerase. Use of this term should not be taken as limiting the scope of the invention to libraries of polynucleotides which are actually used as templates in a subsequent enzyme-catalysed polymerisation reaction.

Use of the Template Library

Template libraries prepared according to the method of the invention may be used in essentially any method of nucleic acid analysis. The libraries are particularly useful in methods of determining a sequence characteristic of one or more portions of a polynucleotide sequence. Exemplary methods for determining a sequence characteristic include, but are not limited to sequencing, genotyping, copy number variation analysis, gene expression analysis, DNA methylation analysis and the like. For purposes of illustration the method of the invention is exemplified below in sequencing embodiments. Those skilled in the art will recognize that the methods can be similarly applied to prepare genomic DNA samples for genotyping methods such as those described in US 2005/0181394 or US 2003/0108900, each of which is incorporated herein by reference; detection of copy number variation, or methylation analysis methods such as those described in US 2003/0170684, which is incorporated herein by reference.

The template libraries produced by the methods set forth herein are particularly useful for analysis methods which employ further simplification of the templates. Exemplary uses of the template libraries include, but are not limited to, providing templates for solid-phase amplification (of either monotemplate or complex template libraries). For example the library may be: dispersed into an emulsion for amplification on individual beads, or may be used to form an array of clusters on a single planar solid support. A particularly preferred use is in solid-phase isothermal amplification carried out on a solid-support as described in further detail below.

Whole-Genome Amplification

Template libraries containing fragment polynucleotide sequences prepared according to the method of the invention starting from a complex mixture of genomic DNA fragments representing a whole or substantially whole genome provide suitable templates for so-called "whole-genome" amplification. The term "whole-genome amplification" refers to a nucleic acid amplification reaction (e.g. PCR) in which the template to be amplified comprises a complex mixture of nucleic acid fragments representative of a whole (or substantially whole genome). Exemplary methods of amplification that can be used to make copies of polynucleotide fragments generated by a method set forth herein or to prepare a polynucleotide sample for fragmentation in the methods of the invention include, but are not limited to, rolling circle amplification, linker adapter PCR, multiplex PCR, random primer amplification, polony amplification, bridge PCR, emulsion PCR and other methods known in the art. Several useful amplification methods that can be used are described in U.S. Ser. No. 11/943,554; US 2005/0181394 or US 2003/0108900, each of which is incorporated herein by reference.

Arrays

Determining a sequence characteristic of a sample using polynucleotide fragments produced by the methods set forth herein can be carried out using essentially any type of array formed by immobilisation of nucleic acid molecules on a solid support, and more particularly any type of high-density array, including single molecule, amplified single molecule (cluster) arrays, arrays of beads on which molecules have been amplified (for example in an emulsion PCR reaction), or arrays of beads on which amplified molecules have been hybridised.

As used herein, the term "array" refers to a population of different molecules that are attached to one or more substrates such that the different molecules can be differentiated from each other according to relative location. An array can include different probe molecules, such as polynucleotide fragments, that are each located at a different addressable location on a substrate. Alternatively, an array can include separate substrates each bearing a different probe molecule. Probes attached to separate substrates can be identified according to the locations of the substrates on a surface to which the substrates are associated or according to the locations of the substrates in a liquid.

Exemplary arrays in which separate substrates are located on a surface include, without limitation, those including beads in wells. Arrays useful in the invention are described, for example, in U.S. Pat. Nos. 6,023,540, 6,200,737, 6,327,410, 6,355,431, 6,482,593 and 6,429,027; U.S. patent application publication Nos. U.S. 2002/0102578 and US 2006/0275782A1, each of which is incorporated herein by reference. Further examples of arrays that can be used in the invention are photolithographic arrays such as GeneChip™ arrays available from Affymetrix, spotted arrays such as CodeLink™ arrays available from Applied Microarrays. Commercially available fluid formats for distinguishing beads include, for example, those used in xMAP™ technologies from Luminex.

Because the fragments prepared using the methods of the present invention are generally substantially uniform in size, they are particularly suitable for sequencing methods that obtain reads from both ends of each fragment. In multi-polynucleotide or clustered arrays distinct regions on the array comprise multiple copies of single polynucleotide template molecules. Multi-polynucleotide or clustered arrays of nucleic acid molecules may be produced using techniques generally known in the art. By way of example, US 2005/0100900 and U.S. Pat. No. 7,115,004, the contents of which are incorporated herein by reference, both describe methods of nucleic acid amplification where the amplification products take the form of arrays comprised of clusters or "colonies" of immobilised nucleic acid molecules. The arrays are amplified such that both strands of a duplex are immobilised, but cleavage of one of the strands from the surface (for example using a chemical and/or a subsequent heat treatment to cleave and denature one of the amplification primers used to generate the copies of the immobilised single molecules), results in an array of single stranded templates suitable for sequencing. Methods for the linearization and sequencing of DNA clusters are described in co-pending application WO07010251, the contents of which are incorporated herein by reference.

The method of the invention may also be used in the preparation of sequencing templates for single molecule arrays of nucleic acid templates. Single molecule arrays are generally formed by immobilisation of single polynucleotide molecules at discrete sites that are detectable on the array. Single-molecule arrays comprised of nucleic acid molecules that are individually resolvable by optical means and the use of such arrays in sequencing are described, for example, in US 2005/0042649, the contents of which are incorporated herein by reference.

Sequencing

Any suitable method of sequencing may be used to determine a sequence read of the fragments prepared using the present invention. Suitable methods of sequencing include the use of sequencing by addition of nucleotide bases, for example sequencing by synthesis (SBS) using nucleoside triphosphates and DNA polymerases (as described in US 2007/0166705 and US 2006/0240439 respectively), or using oligonucleotide cassettes and ligases (as described in U.S. Pat. No. 6,306,597, US 2008/0003571 or Science, 309:5741, 1728-1732 (2005)). The fragments may also be sequenced by pyrosequencing (Nature. 437:376-380 (2005)), or by MPSS where the strands are degraded rather than extended (Nat Biotechnol. 6:630-6344 (2000)). All the documents cited in this paragraph are incorporated herein by reference.

In "sequencing by synthesis" or SBS a new polynucleotide strand base-paired to a template strand is built up in the 5' to 3' direction by successive incorporation of individual nucleotides complementary to the template strand. In one embodiment of SBS the substrate nucleoside triphosphates used in the sequencing reaction are each labelled son the base with different labels permitting determination of the identity of the incorporated nucleotide as successive nucleotides are added. The labelled nucleoside triphosphates also have a 3' blocking group which prevents further incorporation of complementary bases by the polymerase. The label of the incorporated base can then be determined and the blocking group removed to allow further polymerisation to occur. Labelled nucleotides for use in the inventions are described in WO07135368, whose contents are incorporated by reference herein.

Further provided herein are methods of sequencing multiple nuclei-c acid molecules in parallel based on the use of arrays, wherein multiple template molecules immobilised on the array are sequenced in parallel. Such arrays may be single molecule arrays or arrays having populations of molecules at each feature such as clustered arrays. In particularly useful sequencing embodiments, nucleotide(s) is(are) incorporated into a strand of nucleic acid complementary to the template nucleic and each nucleotide is fluorescently labelled. The inclusion of a fluorescent label facilitates detection/identification of the base present in the incorporated nucleotide(s). Appropriate fluorophores are well known in the art several of which are described in further detail below.

The labels may be the same for each type of nucleotide, or each nucleotide type may carry a different label. This facilitates the identification of incorporation of a particular nucleotide. Thus, for example modified adenine, guanine, cytosine and thymine would all have attached a different fluorophore to allow them to be discriminated from one another readily. When sequencing on arrays, a mixture of labelled and unlabelled nucleotides may be used. Detectable labels such as fluorophores can be linked to nucleotides via the base using a suitable linker. The linker may be acid labile, photolabile or contain a disulfide linkage. Preferred labels and linkages include those disclosed in U.S. Pat. No. 7,057,026. Other linkages, in particular phosphine-cleavable azide-containing linkers, may be employed in the invention as described in greater detail in US 2006/0160081. The contents of U.S. Pat. No. 7,057,026 and US 2006/0160081 are incorporated herein by reference.

The nucleotides described in US 2006/0160081 comprise: a purine or pyrimidine base and a ribose or deoxyribose sugar moiety which has a removable blocking group covalently attached thereto, preferably at the 3'O position. 3' blocking groups are also described in US 2007/0166705, the contents of which are also incorporated herein by reference. Use of such 3'-blocked nucleotides permits controlled incorporation of nucleotides in a stepwise manner, since the presence of a blocking group at the 3'-OH position prevents incorporation of additional nucleotides. The detectable label may, if desirable, be incorporated into the blocking groups as is disclosed in US 2007/0166705.

In further embodiments of SBS or cycle sequencing wherein the substrate nucleoside triphosphates used in the sequencing reaction are each labelled on the base with the same label and/or wherein the labelled nucleoside triphosphates do not have a 3' blocking group to prevent further incorporation of complementary bases by the polymerase it will be apparent to the skilled person that in these cases the nucleotides can be supplied individually and serially and incorporation of a base can then be determined before applying the next nucleotide.

Methods for detecting fluorescently labelled nucleotides generally require use of incident light (e.g. laser light) of a wavelength specific for the fluorescent label, or the use of other suitable sources of illumination, to excite the fluorophore. Fluorescent light emitted from the fluorophore may then be detected at the appropriate wavelength using a suitable detection system such as for example a Charge-Coupled-Device (CCD) camera, which can optionally be coupled to a magnifying device, a fluorescent imager or a con focal microscope. If sequencing is carried out on an array, detection of an incorporated base may be carried out by using a scanning microscope to scan the surface of the array with a laser, to image fluorescent labels attached to the incorporated nucleotide (s). A sensitive 2-D detector, such as a charge-coupled detector (CCD), can be used to visualise the signals generated. This technique is particularly useful with single molecule arrays.

Other techniques such as scanning near-field optical microscopy (SNOM) are available and may be used when imaging dense arrays. For a description of scanning near-field optical microscopy, see Moyer et al., Laser Focus World 29:10, 1993. An additional technique, that may be used is a surface-specific total internal reflection fluorescence microscopy (TIRFM) see, for example, Vale et al., Nature, (1996) 380:451-453.

Suitable apparatus used for imaging polynucleotide arrays are known in the art and the technical set-up will be apparent to the skilled person. Detection buffers containing antioxidants, such as sodium ascorbate, show a clear improvement (over corresponding buffers absent such antioxidants) at preventing light-induced chemical artefacts in cycles of sequencing-by-synthesis based on detection of fluorescently labelled nucleotide analogues, as described in WO06064199. The inclusion of antioxidants prevents/reduces light-induced chemical reactions from damaging the integrity of the nucleic acid template and allows accurate determination of the identity of the incorporated base over at least 12, preferably at least 25 and more preferably at least 36 cycles of nucleotide incorporation.

Preferably from 10 to 50 or more are successively incorporated, and identified in the sequencing reaction. The ability to accurately sequence 20 or more consecutive nuclectides in a sequencing reaction is a significant advantage in applications such as genome re-alignment. In the context of the methods described herein sequencing includes any polynucleotide "sequencing-by-synthesis" reaction which involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced.

The identity of the base present in one or more of the added (oligo)nucleotide(s) is determined in a detection or "imaging" step. The identity of the added base is preferably determined after each nucleotide incorporation step. The sequence of the template may then be inferred using conventional Watson-Crick base-pairing rules. Instruments suitable for imaging an array of nucleic acid clusters comprising incorporated labelled nucleotides is described in WO07123744, the contents or which are incorporated by reference herein.

The nucleic acid template to be sequenced in a sequencing reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The primer bearing the free 3' hydroxyl group may be added as a separate component (e.g. a short oligonucleotide) which hybridises to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added may be determined, thus providing sequence information for the nucleic acid template.

The term "incorporation" of a nucleotide into a nucleic acid strand (or polynucleotide) refers to joining of the nucleotide to the free 3' hydroxyl group of the nucleic acid strand via formation of a phosphodiester linkage with the 5' phosphate group of the nucleotide. The nucleic acid template to be sequenced may be DNA or RNA, or even a hybrid molecule comprised of deoxynucleotides and ribonucleotides. The nucleic acid may include naturally occurring and/or non-naturally occurring nucleotides and natural or non-natural backbone linkages.

Nucleic acid templates to be sequenced may be attached to a solid support via any suitable linkage method known in the art. Preferably linkage will be via covalent attachment. If the templates are "arrayed" on a solid support then the array may take any convenient form. Thus, the method of the invention is applicable to the preparation of nucleic acid fragments for the production of all types of "high density" arrays, particularly single-molecule arrays and clustered arrays.

Single molecule arrays comprised of individually resolvable nucleic acid molecules including a hairpin loop structure are described in U.S. Pat. No. 6,787,308, which is incorporated herein by reference. The methods of the invention are suitable for the preparation of template molecules for single molecule arrays prepared according to the disclosures of US 2005/0042649 or U.S. Pat. No. 6,787,308, each of which is incorporated herein by reference. The fluorescent moiety may be attached to a nucleic acid via any su table: covalent or non-covalent linkage. For example, the fluorescent moiety may be attached to an oligonucleotide primer or probe which is hybridised to a target nucleic acid molecule.

Preferably a large number of template sequences are sequenced in parallel at the same time. More preferably greater than 100 template sequences are sequenced at a time. More preferably greater than 1000 template sequences are sequenced at one time, still more preferably greater than 10,000 template sequences are sequenced at one time. Still yet more preferably greater than 100,000 template sequences are sequenced at one time.

One advantage of controlling the length of the fragments is in methods involving paired end reads. Methods for obtaining paired end reads on nucleic acid clusters are described in applications WO07010252, WO07091077 and PCT GB2007/003798, the contents of which are incorporated herein by reference.

One method of obtaining paired end reads on an array of clusters involves strand resynthesis between the first and second read. The method is described in full in PCT GB2007/0073798, but is summarised below. Upon amplification of the template strands, a bridged double stranded structure is produced. This can be treated to release a portion of one of the strands of each duplex from the surface. The single stranded nucleic acid is available for sequencing primer hybridisation and cycles of primer extension. After the first sequencing run, the ends of the first single stranded template can be hybridised to the immobilised primers remaining from the initial cluster amplification procedure. The immobilised primers can be extended using the hybridised first single strand as a template to resynthesize the original double stranded structure. The double stranded structure can be treated to remove at least a portion of the first template strand to leave the resynthesized strand immobilised in single stranded form. The resynthesized strand can be sequenced to determine a second read, whose location originates from the opposite end of the original template fragment obtained from the fragmentation process.

Example

Experimental Overview

The following experimental details describe one embodiment of the invention as described above.

Figure 2:
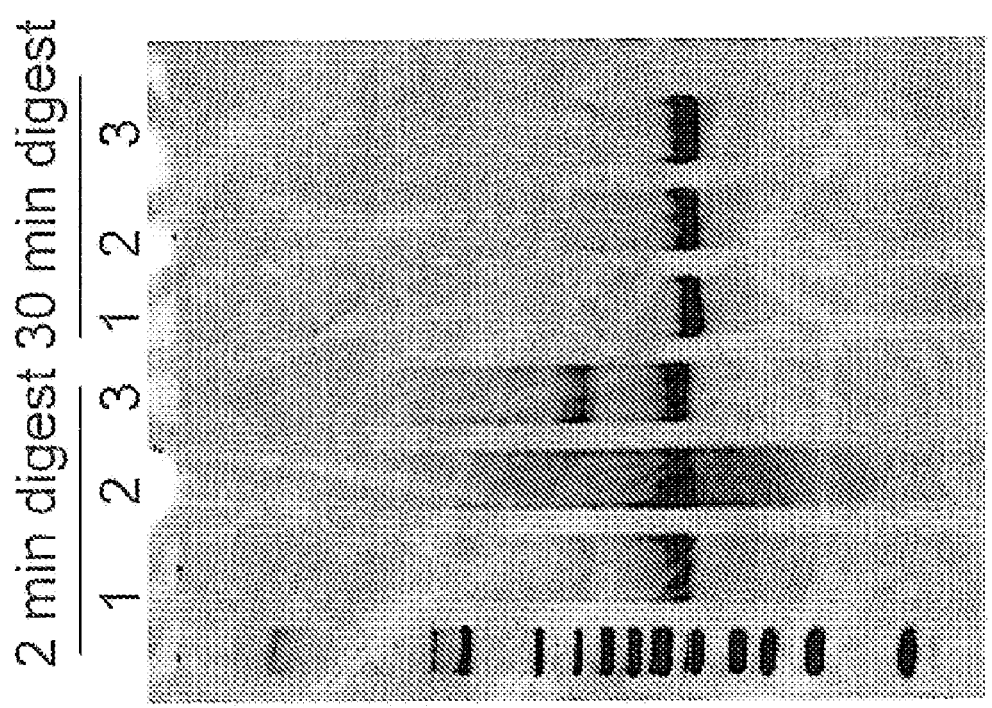
FIG. 2 shows that uniformly sized fragments can be obtained from a variety of DNA sources, both Phi-X and mouse whole genomic DNA samples

The protocols for the chromatin assembly and digestion were supplied by Active Motif as part of their Chromatin Assembly Kit, product number 53500, as used as described. The protocols below are available from the website Activemotif.com The steps in the process involve chromatin assembly, digestion with an enzyme cocktail containing micrococcal nuclease, then digestion of the nucleosomes with proteinase K. The nucleic acid samples were run down an agarose gel (FIG. 2). Two sets of three samples were digested. The first set was digested for 2 minutes with the enzyme cocktail and the second set was digested for 30 minutes. Both sets included different DNA samples identified in FIG. 2 as (1) 2 micrograms Phi-X DNA, (2) 1.7 micrograms mouse genomic DNA and (3) 0.85 micrograms mouse genomic DNA). Samples two and three from the 30 minute digestion were gel purified, sample 1 was used directly and all three were theft used for sequencing analysis as follows. The nucleic acid samples were end repaired, ligated into a vector, cloned and sequenced using standard protocols. The sequencing results showed the spread of fragment lengths obtained with each fragmentation method, and is shown in FIG. 3. Whilst the gel free method gives the broadest spread of fragment lengths, the advantage is that all of the sample is contained in this narrow range. Gel excision gives tighter bands, depending on how narrow the user cuts the slices, but the majority of the sample remains in the gel and is lost.

The samples obtained herein are suitable for adapter ligation and cluster formation, as described in US 2007/0128624 and US 2008/0009420 respectively, the contents and protocols described therein being incorporated herein by reference.

The invention claimed is:

1. A method for preparing and analysing a population of fragmented polynucleotide sequences having a substantially uniform size comprising:
   (a) binding at least one protection molecule to at least one polynucleotide sequence;
   (b) cleaving the at least one polynucleotide sequence to generate a plurality of polynucleotide fragment sequences of substantially uniform size;
   (c) amplifying the polynucleotide fragments, wherein the amplification is performed on a solid support, wherein the amplification produces an array of locations, each location comprising multiple copies amplified from a single template; and
   (d) sequencing the polynucleotide fragments, wherein a strand of each of the templates is sequenced, the strand of each of the templates is converted into a double stranded template using strand resynthesis, and wherein the resynthesized template is used for a second round of sequencing, thereby analysing a population of fragmented polynucleotide sequences having a substantially uniform size.

2. The method according to claim 1 wherein both ends of the fragment are analysed in a paired end sequencing procedure.

3. The method according to claim 1 wherein the at least one protection molecule is a histone or a DNA binding protein.

4. The method according to claim 3 wherein in step (b) the at least one polynucleotide sequence is cleaved by mechanical, chemical or enzymatic means.

5. The method according to claim 4 wherein the cleaving is by enzymatic means.

6. The method according to claim 5 wherein the enzymatic means is micrococcal nuclease.

7. The method according to claim 1, wherein the solid support is a pool of beads or microspheres.

8. The method according to claim 1, wherein the solid support is an planar surface.

9. The method according to claim 1, wherein the strand resynthesis is performed using multiple cycles of hybridisation, extension and denaturation.

10. The method according to claim 1, wherein the strand resynthesis is performed isothermally.

11. The method according to claim 1, further comprising removing the protection molecule from the polynucleotide fragment sequences after the cleaving.

12. The method according to claim 1, further comprising attaching universal adapter sequences to the ends of each polynucleotide fragment.

13. The method according to claim 12, wherein the amplifying of the polynucleotide fragments comprises using the universal adapter sequences as sites for primer hybridization.

14. The method according to claim 12, wherein the multiple copies produced by the amplifying are double stranded copies, and wherein the method further comprises making each of the double stranded copies into the single stranded template by removing at least a portion of one of the strands from the surface.

15. The method according to claim 1, wherein the plurality of polynucleotide fragment sequences comprises a sequence representation that includes the entire sequence complement of a genome from a particular organism.

16. The method according to claim 15, wherein the organism is a human.

17. The method according to claim 7, wherein the amplifying comprises emulsion PCR.

18. The method according to claim 1, wherein the multiple copies produced by the amplifying are double stranded copies, and wherein both strands of the double stranded copies are attached to the solid support.

19. The method according to claim 1, wherein greater than 100 of the polynucleotide fragments are sequenced in parallel on the solid support.

* * * * *